(12) United States Patent
Forrester

(10) Patent No.: US 9,436,800 B2
(45) Date of Patent: Sep. 6, 2016

(54) METHOD AND SYSTEM FOR COLLECTING AND DISSEMINATING DATA PRODUCED BY MEDICAL DEVICES, PARTICULARLY THOSE USED IN INTENSIVE CARE UNITS

(75) Inventor: Steven Forrester, Paris (FR)

(73) Assignee: CAPSULE TECHNOLOGIE, Paris (FR)

( * ) Notice: Subject to any disclaimer, the term of this patent is extended or adjusted under 35 U.S.C. 154(b) by 2084 days.

(21) Appl. No.: 10/258,244

(22) PCT Filed: Apr. 5, 2001

(86) PCT No.: PCT/FR01/01036
§ 371 (c)(1),
(2), (4) Date: May 6, 2003

(87) PCT Pub. No.: WO01/77981
PCT Pub. Date: Oct. 18, 2001

(65) Prior Publication Data
US 2003/0200116 A1  Oct. 23, 2003

(30) Foreign Application Priority Data
Apr. 6, 2000  (FR) ..................................... 00 04391

(51) Int. Cl.
*G06Q 50/00* (2012.01)
*G06F 19/00* (2011.01)
(Continued)

(52) U.S. Cl.
CPC ........... *G06F 19/327* (2013.01); *G06F 19/321* (2013.01); *G06F 19/3406* (2013.01);
(Continued)

(58) Field of Classification Search
CPC ...... G06Q 50/22; G06Q 50/24; G06Q 40/08; G06Q 10/10; G06F 19/322
USPC ............................................................. 705/2
See application file for complete search history.

(56) References Cited

U.S. PATENT DOCUMENTS 4,653,112 A   3/1987  Ouimette
4,764,870 A   8/1988  Haskin
(Continued)

FOREIGN PATENT DOCUMENTS

WO   WO 99/41691   8/1999

OTHER PUBLICATIONS

Final Office Action for U.S. Appl. No. 10/257,098, mailed Nov. 6, 2012.
(Continued)

*Primary Examiner* — Tran Nguyen
(74) *Attorney, Agent, or Firm* — The Marbury Law Group, PLLC

(57) ABSTRACT

The invention relates to a method and a system for collecting medical data produced by medical devices (1) situated, for example, in intensive care units and for disseminating said information to the health professionals using computer equipment (5).
The process and the system include the following software modules:
(I) one service module (DS) (21),
(II) a data storage module (DDS) (25),
(III) control modules (DAC) (26) accessible from any point of said computer communications network and controlling the distribution of said data D,
(IV) a device interface module (DDI) (23), configured as a function of the specifications of said transmitter devices (1),
(V) a communications interface module (DCI) (22),
(VI) a configuration interface module (DCP) (28),
(VII) a data portal module (DDP).

10 Claims, 2 Drawing Sheets

Figure 1:
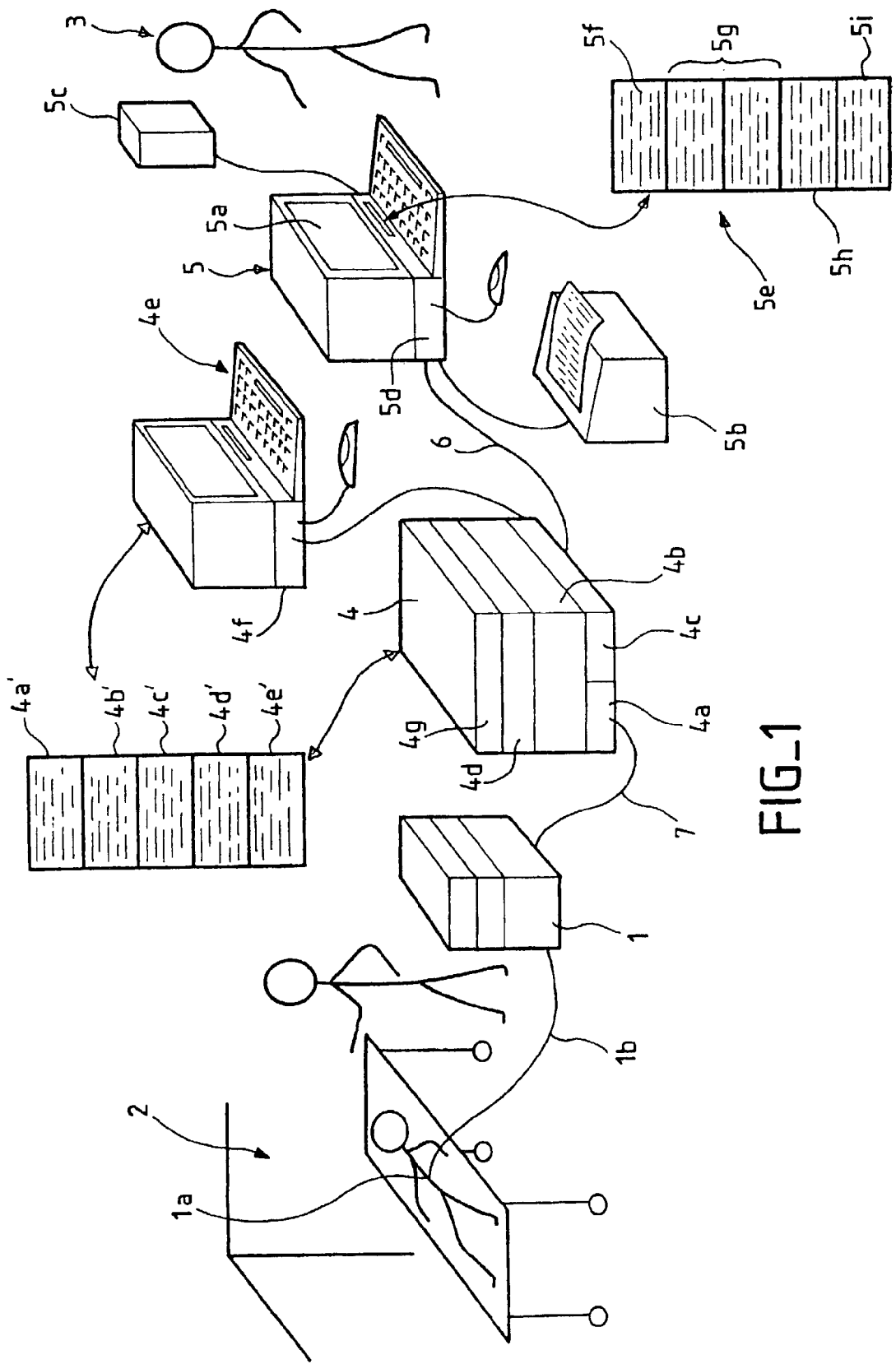

(51) Int. Cl.
   *G06Q 50/22* (2012.01)
   *G06Q 10/00* (2012.01)

(52) U.S. Cl.
   CPC ....... *G06F19/3418* (2013.01); *G06F 19/3425* (2013.01); *G06Q 50/22* (2013.01); *G06F 2213/0002* (2013.01)

(56) References Cited

U.S. PATENT DOCUMENTS

| | | | |
|---|---|---|---|
| 5,513,101 A | | 4/1996 | Pinsky et al. |
| 5,664,109 A | * | 9/1997 | Johnson et al. ................... 705/2 |
| 5,715,823 A | | 2/1998 | Wood et al. |
| 5,822,544 A | | 10/1998 | Chaco et al. |
| 5,890,129 A | | 3/1999 | Spurgeon |
| 5,995,937 A | * | 11/1999 | DeBusk et al. ................... 705/2 |
| 6,018,713 A | | 1/2000 | Coli |
| 6,074,345 A | * | 6/2000 | van Oostrom ....... A61B 5/0002 128/904 |
| 7,447,643 B1 | * | 11/2008 | Olson et al. ...................... 705/2 |
| 2002/0031243 A1 | * | 3/2002 | Schiller et al. ............... 382/119 |
| 2003/0158746 A1 | | 8/2003 | Forrester |

OTHER PUBLICATIONS

Office Action for U.S. Appl. No. 10/257,098, mailed Mar. 28, 2012.
Final Office Action for U.S. Appl. No. 10/257,098, mailed May 13, 2011.
Office Action for U.S. Appl. No. 10/257,098, mailed Aug. 19, 2010.
Final Office Action for U.S. Appl. No. 10/257,098, mailed Mar. 6, 2009.
Office Action for U.S. Appl. No. 10/257,098, mailed Apr. 4, 2008.
International Search Report—PCT/FR2001/001036—ISA/EPO—Jul. 12, 2001.
Kleinholz L., et al., "Multimedia and Pacs Setting The Platform and Improved and New Medical Services an Hospitals and Regions", Computer Assisted Radiology, Proceedings of the International Symposium on Computer and Communication Systems for Image Guided Diagnosis and Therapy, Jun. 1996, pp. 313-322, XP002083080.

* cited by examiner

FIG_1

METHOD AND SYSTEM FOR COLLECTING AND DISSEMINATING DATA PRODUCED BY MEDICAL DEVICES, PARTICULARLY THOSE USED IN INTENSIVE CARE UNITS

This invention relates to a novel method and a novel system for collecting data produced by transmitter devices producing said data and for disseminating same to users. Each user has at least one data processing device, namely a personal computer, connected to a monitor and/or a printer and/or to a speaker. Each computer is associated with data analysis software.

More particularly, the invention relates to a novel method and a novel system for collecting data produced by medical devices, namely originating from medical apparatus used in intensive care units, and disseminating said data to health care workers. Each health care worker has access to at least one data processing device, namely a personal computer, connected to a monitor and/or to a printer and/or to a speaker. Said data processing device is associated with software for analyzing clinical data.

The medical apparatus currently used in intensive care units include: cardiac monitors, ventilators, infusion pumps, etc. The majority of equipment available on today's market are equipped with a communications port, generally an RS232 port. They allow dissemination of all or part of the data collected to clinical analysis software. Said software use the data collected by the medical devices for several applications; for studying the patient's reaction to a treatment or to a prescription change, for example. This is clearly important information for the whole medical community, from the physician and nursing staff to the hospital administration, pharmaceutical companies and the managers of the national health plan.

Here, a fundamental problem must be solved if one wishes to call up data collected by the medical devices. In fact, there is no common communications protocol among such devices and computers. By using a simple analogy, each medical device speaks a language that is unique to itself; therefore, each software must speak and understand a multitude of languages.

There are essentially two ways to solve this problem.

The first solution consists of connecting each medical device to a black box that is specific to it and which is designed to translate the messages received into a common language that can be understood by the clinical software. By way of example, Device Link manufactured by HP or Marquette-Hellige's Octanet can be mentioned.

The second solution consists of developing for each clinical analysis software a program that is specific to each medical device. By way of example, the clink'n link solution manufactured by Picis and HP's CareVue can be mentioned.

The one or the other instance, the diversity of devices and the software developed requires black box designers and/or developers of clinical software to continuously modify their products without meeting the needs of those consumers already using equipment. The solutions disclosed in EASTMAN KODAK (WO 99 41691 A) dated Aug. 19, 1999, WOOD et al. (U.S. Pat. No. 5,715,823) dated Feb. 10, 1998, KLEINHOLZ et al. (XP00208380) of June 1996, HASKIN MARVIN E (U.S. Pat. No. 4,764,870 A) of Aug. 16, 1998 and PINSKY et al. (U.S. Pat. No. 5,513,101 A) dated Apr. 30, 1996 present the same drawbacks.

Of course, there have certainly been attempts made to standardize the messages output by the devices. To date, those attempts have not produced results. So, for example, it required several years to produce the first draft for standardization of information generated by infusion pumps, one of the simplest devices on the market.

The method according to the invention is a method for collecting data D produced by transmitter devices generated by medical devices such as those used in intensive care units. Said method is conceived also for disseminating said data D to the users; that is, to the healthcare workers. Each user has at least one data processing equipment, namely a personal computer, connect to a monitor and/or a printer and/or speakers. Each data processing device is connected to a data analysis software, namely clinical analysis software. The data are provided by the transmitter equipment according to the different specific formats corresponding to the types of transmission equipment. The method according to the invention includes software modules, hereinafter specified that carry out the steps of the method.

The DataCaptor (DS) service module activates and controls the function of the other modules.

The DataCaptor data storage module (DDS) stores the data D and the commands C, namely on a disk.

The DataCaptor activeX control modules (DAC) are accessible from all points on the data processing communications network and control the dissemination of said data D.

Each DAC module received the data D from the associated DDS modules and transmits them via the data processing communications network to the data processing equipment and the data analysis software; that is, to the clinical analysis software. Each DAC modules addresses the commands C to all or only a part of the other modules.

The DataCaptor interface module (DDI) is configured as a function of the specifications of said transmitter devices connected to the data processing communications network in order to establish and maintain a connection with said transmitter devices via a DataCaptor communications interface module (DCI). The DDI modules transmit the collected and translated data (D) using a common format to the storage module DDS for said data D.

The DataCaptor communications interface module (DCI) activates and controls the physical communications ports to the data processing communications network to which said transmitter devices are connected.

The DataCaptor configuration interface (DCP) is employed by the user for specifying:
the physical branches between the transmitter devices and the physical communications ports,
the communications parameters,
the identifiers of said transmitter devices concerned.

Advantageously, the method according to the invention is such that each DCI module can be activated by any one of said DataCaptor DDI interface modules and is activated by said DDI module, which requires, for the first time, said physical communications port.

Thus, each transmitter device associated with a DDI module and connected to said data processing communications network via a DCI module can exchange data D and/or commands C with any one of said data processing devices.

According to one variant embodiment, the process is such that each DAC module receiving said data D from the associated DDS modules transmits said data D via a DataCaptor data port module (DDP) to said data processing equipment. The DDP module converts the data D to the communications format of the data analysis software and transmits the data, converted in this fashion, to the concerned user's data processing equipment.

Preferably, the DS module maintains the integrity and security of the method and transmits the data D.

Also preferably, the DDS processes the requests for historical data.

Further preferably, the DDS provides the other user interface modules with the data D and the commands C.

According to a variant embodiment, the DAC module is integrated into the data analysis software by the programmer of said data analysis software.

Also preferably, the DDI module simultaneously assures high-level communications relative to the communications protocols of the data transmitted by the transmitter devices and the low-level communication by means of the DCI modules.

Further preferably, The DDI module reads and translates the occasional parameters and/or the data curves being output from said transmitter devices.

Also preferably, there are as many DCI modules as they are types of communications ports.

Also preferably, the DCP module allows updating of a directory.

Also preferably, the DCP module provides the DCI modules with information relative to the transmitter devices.

Figure 2:
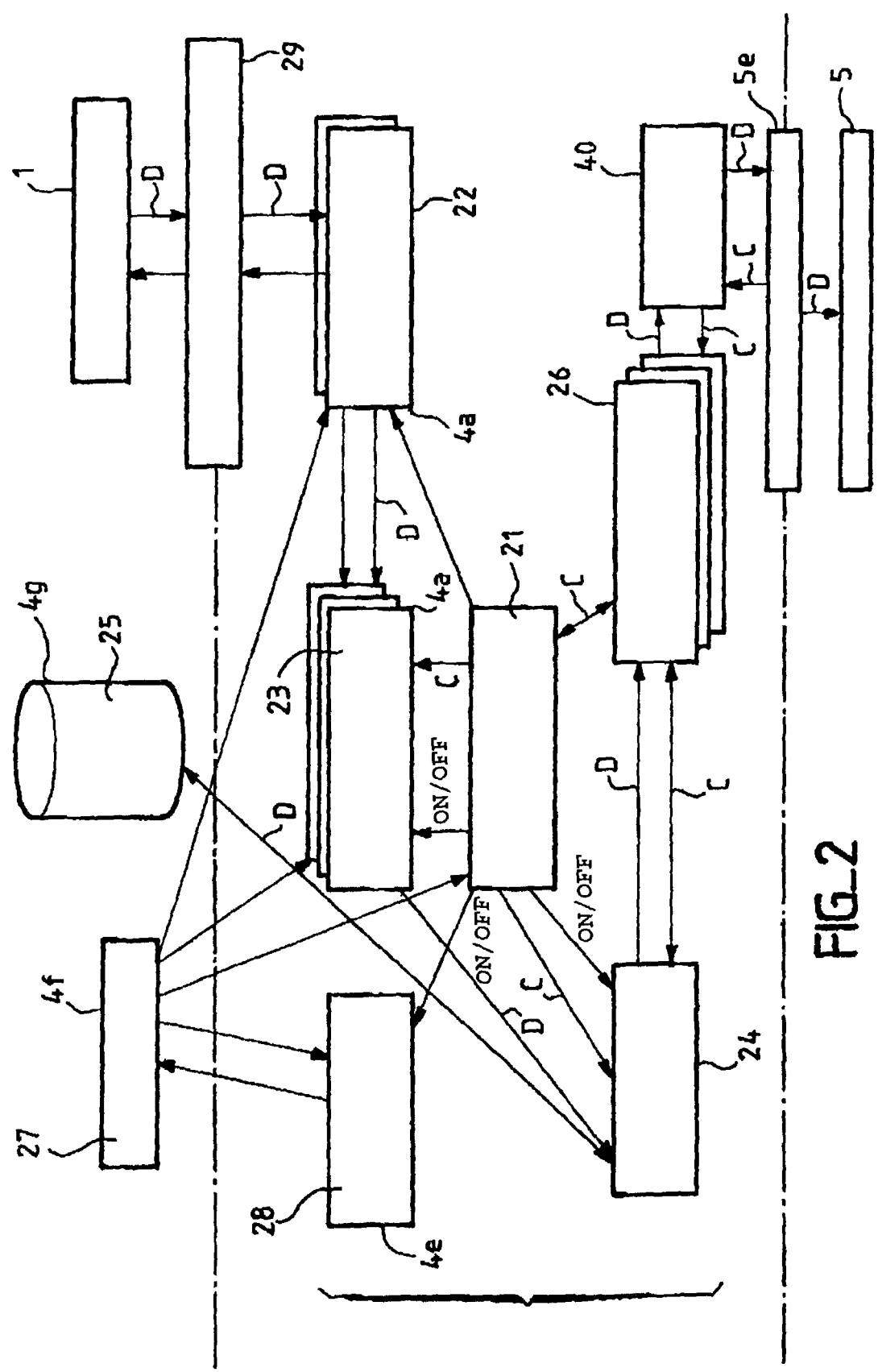

Other characteristics and advantages of the invention will be obvious when reading the disclosure of variant embodiments of the invention that are provided by way of example, but not limitingly, and of:

FIG. 1 that schematically represents a variant embodiment of the system according to the invention, FIG. 2 that schematically represents in block-diagram form the six modules comprising a variant embodiment of the software that allows implementation of the invention.

A variant embodiment of the system according to the invention will now be described in illustrative fashion in a case, wherein the transmitter devices are medical devices.

The system is designed for collecting medical data generated by medical devices 1. These medical devices are, for example, situated in intensive care units 2. The system is also designed for disseminating said data to healthcare workers 3.

The system is comprised of at least on data processing device 4. Said data processing device 4 comprises means for receiving 4a; that is a receiving software module 4a', for receiving the data coming 7 from the transmitter devices 1. Said data processing device 4 comprises data processing means 4b; namely, a data processing software module 4b' for translating the data received into a common format. The data processing device 4 comprises also the means for transmitting the data 4c; namely, a data transmission software module 4c' for disseminating the data in the common format to the users 3. The software modules 4a', 4b', and 4c' are represented in FIG. 1 by machine instruction lines. The user 3 has a data processing device 5; namely, a personal computer connected to a displaying monitor 5a. It can also comprise a printer 5b and/or speakers 5c. Each data processing device 5 comprises means for receiving 5d the data transmitted by said data processing device 4, a data analysis software 5e, represented in FIG. 1 by machine instruction lines.

In the case of certain variant embodiments (not represented in FIG. 1), said data processing device 4 can be integrated into the computing equipment 5.

In the case of the variant embodiment represented in FIG. 1, the receiving means 5d of said computing equipment 5 are interconnected by means of a transmitting means 4c of said data processing device 4 over a data processing communications network 6; namely, an Internet type network.

The data analysis software 5e of the computing equipment 5 comprises a conversion module 5f for converting the data according to a common format into the formatted data that is compatible with the computing equipment 5 and/or the other modules 5g of said data analysis software.

In other variant embodiments, the data processing device 4 can comprise additional converting means 4d; namely, a conversion software module 4d' for converting the data according to the common format into the formatted data compatible with the computing equipment 5 and/or its data analysis software 5e.

The data processing device 4 comprises a receiving-configuration interface 4e that allows configuration data entry for the receiving means 4a as a function of the format of the data coming from the transmitter devices 1. The data treatment device 4 comprises a directory 4f containing said configuration data of the receiving means 4a.

The data processing device 4 comprises storage means 4g for storing the translated data in a common format.

The data analysis software 5e of said computing equipment 5 comprises a configuration-receiving software means 5h allowing entry of the configuration data of the receiving means 5d as a function of the specifications of the computing equipment 5 and/or of the other modules 5g of the data analysis software 5e.

The data analysis software 5e also comprises a recording module 5i containing said configuration-receiving data of the receiving means 5d.

By virtue of this combination of means, the users can access the data transmitted by a remote transmitter device, even if those data are formatted according to standards other than those of the users' computing equipment and of the data analysis software that they are using. Moreover, updates are done once for all of the devices and all of the software being used.

In another variant embodiment, the data processing device 4 comprises a transmission-configuration interface 4e; namely, a transmission configuration module 4e allowing entry of configuration data for the transmitting means 4c as a function of the specifications of the computing equipment 5 and of the data analysis software 5e for which they are destined. I this case, the directory 4f contains said configuration data of the transmitting means 4c.

Thus, in the case of this variant embodiment, by virtue of this combination of means, the users can also access the data transmitted by a remote transmitting device even if those data are formatted according to standards other than those of the users' computing equipment and of the data analysis software that they are using. Moreover, updates are done once for all of the devices and all of the software being used.

FIG. 2, a schematic represent a block diagram, will now be described wherein the six modules comprising a variant embodiment of the software allowing implementation of the invention. The software, hereinafter called the "DataCaptor" software, is comprised of the following 7 modules:

The DataCaptor service (DS) 21, otherwise known in French as le Service DataCaptor, is the heart of the software. It starts up and controls the other modules. It assures the correct function of the entire system. It detects malfunctions and restores normal function by correcting any problems. It verifies that each DataCaptor Communications Interface (DCI) module 22 (4a, FIG. 1), otherwise known in French as the Interface de Communication de DataCaptor, is activated and is functioning correctly. It maintains the integrity and the security of the system at all times. It controls the DataCaptor Device Interface (DDI) 23 (4a, FIG. 1) modules, otherwise known in French as the Interface d'Appareil de DataCaptor, via interfaces (run/stop; On/Off, commands: C). It makes available the interfaces destined for use by the other modules.

The DataCaptor Data Store (DDS) 24, otherwise known in French as the Dispositif de Stockage de Données Data- Captor, is a data storage module D, both for long-term and short-term storage. This module receives the data acquired by each DDI 23, it stores them on disk 25 (4g, FIG. 1) and assures data transmission to the DataCaptor ActiveX Controls (DAC) otherwise known in French as the Contrôles ActiveX DataCaptor. The DDS 24 executes functions well-known per se for managing storage of the data. It is optimized in order to simultaneously process, without a reduction in performance, the real-time requests and requests for historical data. It makes available interfaces that allow exploitation of the data D and commands C by the other modules. All of the data collected are stored locally in binary files.

Each DataCaptor ActiveX Control (DAC) 26 can be accessed from all points of the data processing communications network 6, whether it is a small NetBEUI network or the Internet. Each DataCaptor ActiveX Control (DAC) 26 allows dissemination of the data D.

The DataCaptor ActiveX (DAC) 26 finds the relevant DataCaptor Data Store (DDS) 24 whose address it recognizes, then it records itself with it as the data receiver. DataCaptor ActiveX (DAC) 26 can then receive the data D coming from the relevant DataCaptor Data Store (DDS) 24. Said latter can be situated locally or even remotely. The data D are transmitted by the DataCaptor ActiveX (DAC) 26 to the computing equipment 5 (FIG. 1) of the healthcare worker via the DataCaptor Data Portal (DDP) 40, otherwise known in French as the Portail de Données DataCaptor. The clinical software used by a healthcare worker thus accesses all of the data relative to a patient and collected by any medical device in a care unit, a hospital, etc.

The DataCaptor ActiveX (DAC) 26 can address commands C to the DataCaptor Data Store (DDS) 24 and/or to the DataCaptor Service (DS) 21 as well as to any other module.

The programmer of the clinical analytical application software 5e can, in the case of certain variant embodiments, integrate DataCaptor ActiveX (DAC) 26 module in the system. The DataCaptor ActiveX (DAC) 26 is the system utilization interface for the programmer. In the case of this variant, the commands addressed by the DataCaptor ActiveX (DAC) 26 to the DataCaptor Data Store (DDS) 24 and/or to the DataCaptor Service (DS) 21 as well as to any module can be preprogrammed in the application software and actioned by the healthcare worker. By enclosing one or a plurality of DataCaptor ActiveX (DAC) 26 modules in the clinical software used by a healthcare worker s/he can access all of the data relative to a patient and collected by any medical device in a care unit, a hospital, etc.

The DataCaptor Device Interfaces (DDI) 23 permit access to the medical devices via the DataCaptor Communication Interface (DCI) 22. They are configured as a function of the specifications of the connected medical device using the parameters contained in the directory 27 (4f, FIG. 1) of the user system and entered in the directory from the DataCaptor Control Panel (DCP) 28 (4e, FIG. 1), otherwise known in French as the Panneau de Contrôle DataCaptor. They are started up by the DataCaptor Service (DS) 21. Then each dataCaptor Device Interfaces (DDI) 23 connects to the appropriate DataCaptor Communication Interface (DCI) 22. The DataCaptor Device Interfaces (DDI) 23 assure maintenance of the connection with the connected device and manage any communications errors that are detected. Each DataCaptor Device Interfaces (DDI) 23 simultaneously assures the low-level interface using the DataCaptor Communication Interface (DCI) 22 module and the high-level interference the communications protocols of the data transmitted by the concerned medical device. The DataCaptor Device Interfaces (DDI) 23 read and translate the protocols of the medical devices to which they are connected.

The DataCaptor Device Interfaces (DDI) 23 can read and translate the sporadic parameters, the data curves in real time and any other digital datum being output by the medical devices.

Each DataCaptor Device Interfaces (DDI) 23 transmits the collected data to the DataCaptor Data Store (DDS) 24.

The DataCaptor Communication Interface (DCI) 22 allow starting up and controlling the physical communications ports 29 to the data processing communications networks to which the medical devices 1 are connected. There is DataCaptor Communication Interface (DCI) 22 for each type of communications port (series, network, etc.). Each DataCaptor Communication Interface (DCI) 22 is started by the first DataCaptor Device Interfaces (DDI) 23 that requires this type of communications port. They also monitor any communications errors.

The DataCaptor Control Panel (DCP) 28 (4e, FIG. 1) is the interface permitting configuration of the system. By using the DataCaptor Control Panel (DCP) 28 the user can specify (i) the physical branchings between the medical devices and the physical communications ports (ii) the communications parameters and (iii) the type of medical device concerned.

The DataCaptor Control Panel (DCP) 28 allows updating of the directory 27 (4f, FIG. 1). The DataCaptor Control Panel (DCP) 28 module provides the DataCaptor Device Interfaces (DDI) 23, via the directory 27, with the information relative to the configuration of the data sources of the system as well as to the concerned DataCaptor Communication Interface (DCI) 22.

The DataCaptor Data Portal (DDP) 40 is the data D conversion module providing the DataCaptor ActiveX (DAC) 26 with the communications format of the clinical analysis software 5e (FIG. 1). The DataCaptor Data Portal (DDP) 40 transmits the data converted in this fashion to the clinical analysis application software 5e of the computing equipment 5 (FIG. 1). The DataCaptor Data Portal (DDP) 40 receives the commands C from the clinical analysis application software 5e (FIG. 1) and transmits them to the DataCaptor ActiveX Controls (DAC) 26.

A DataCaptor Data Portal (DDP) 40 is destined to receive the data D from one or a plurality of DataCaptor ActiveX Controls (DAC) 26.

When the programmer of the clinical analysis application software 5e (FIG. 1) integrated a DataCaptor ActiveX Controls (DAC) 26 module in the software it is not necessary to provide a DataCaptor Data Portal (DDP) 40. In this case also, the clinical analysis application software 5e programmer adapts the proprietary clinical analysis software language to the common format.

SUMMARY

Analysis of the problem and the solution according to the invention shows that it is possible to split up the overall problem into several simpler problems to be resolved:

Acquiring the data. Management of the communications with the device using its communications protocol.

Translating the input data into an internal format.

Filing the data.

Distribution of the data to the users.

Making the data accessible using the application software (namely, the clinical analysis software).

Translation of the internal format to a general format.

Management of the overall system. Assuring the command functions, the history and control.

The solution according to the invention provides all of the data, regardless of the source format, in an unique output format that is easy to utilize.

The basic platform having been used in the development of an alternative embodiment of the DataCaptor software is Microsoft Distributed Component Object Model ([D]COM).

This alternative embodiment of the DataCaptor software is written in Microsoft C++ and Visual Basic. It implements a ([D]COM) basic architecture under WNT, W98 and W95. The choice of ([D]COM) allows resolution of all of the inter-module communications, inter-PC, and Internet questions and allows assurance of compatibility with the future versions of the Microsoft operating system, while allowing binary compatibility with other operating system systems. In fact, [D]COM is a binary standard.

The possibility also exists for writing other alternative embodiments of the DataCaptor software in CORBA using Java. 90% of platforms can then use DataCaptor.

The invention claimed is:

1. A method for distributing medical data, wherein medical data is generated by different types of medical devices using different communication protocols and translated by a medical data processing device connected to the medical devices by different communication ports into a common format, to processing devices each executing an associated data analysis software, comprising:
    connecting at least one of the medical devices to the medical data processing device via a communication port, using one of multiple communications interface (DCI) modules, each of which activates and controls a communication port type and connects one or more of the medical devices to a communications network;
    receiving, by the medical data processing device, medical data generated by at least one of the medical devices using a communication protocol specific to the at least one of the medical devices, wherein the generated medical data is read using one or more of multiple device interface (DDI) modules, wherein one or more DDI modules connected to one or more of the DCI modules, and wherein each DDI module is configured for a medical device to establish and maintain a connection with a connected medical device;
    translating, by the medical data processing device, the generated medical data from the at least one of the medical devices into the common format, using respective DDI modules, wherein the common format comprises an organization of generated medical data supplied by different types of medical devices, wherein the common format is compatible with clinical data processing applications executing on the processing devices;
    storing, by a storage of the medical data processing device, the medical data and the translated medical data using a Data Store (DDS) module; and
    transmitting, by the medical data processing device, the translated medical data to at least one of the processing devices, using a distribution modules, wherein at least one of the distribution modules is integrated in the associated data analysis software associated with the at least one of the processing devices.

2. A method according to claim 1, further comprising:
    activating at least one of the DCI modules by any one of the DDI modules that requires for a first time one of the communication port, and
    wherein each medical device is connected to said communications network over a DCI module such that an associated DDI module is configured to exchange at least one of the medical data or commands with any one of said processing devices.

3. A method according to claim 1, further comprising:
    converting the medical data to a communications format of the associated data analysis software; and
    transmitting the converted medical data to the any one of the processing devices.

4. A method according to claim 1, further comprising processing, in said DDS module, requests for historical data.

5. A method according to claim 1, wherein each of said DDI modules simultaneously assures:
    communication of the medical data transmitted by the associated one of said medical devices, and low-level communication by using the associated one of the DCI modules.

6. A method according to claim 1 wherein the medical data includes sporadic parameters and/or data curves as output from said medical devices.

7. A method according to claim 1, wherein a DCP module is configured to update a directory of the medical data processing device.

8. A method according to claim 1, further comprising providing the DDI modules, via a directory, information about to the medical devices and to the DCI modules.

9. A method according to claim 1, wherein the medical devices are one or more of: cardiac monitors, ventilators or infusion pumps.

10. The method of claim 1, further comprising configuring physical branchings of the medical devices to the communication ports, medical device identifiers, and respective communication parameters for the medical devices by a Control Panel (DCP) module.

* * * * *